US010711292B2

(12) United States Patent
Masuda et al.

(10) Patent No.: US 10,711,292 B2
(45) Date of Patent: Jul. 14, 2020

(54) METHOD FOR PROMOTING THE SYNTHESIS OF COLLAGEN AND PROTEOGLYCAN IN CHONDROCYTES (71) Applicants: NIPPON ZOKI PHARMACEUTICAL CO., LTD., Osaka (JP); THE REGENTS OF THE UNIVERSITY OF CALIFORNIA, Oakland, CA (US)

(72) Inventors: Koichi Masuda, San Diego, CA (US); Mitsuru Naiki, Hyogo (JP)

(73) Assignees: NIKKON ZOKI PHARMACEUTICAL CO., LTD., Osaka (JP); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1145 days.

(21) Appl. No.: 14/858,396

(22) Filed: Sep. 18, 2015

(65) Prior Publication Data

US 2016/0010135 A1 Jan. 14, 2016

Related U.S. Application Data (62) Division of application No. 13/821,617, filed as application No. PCT/US2011/055757 on Oct. 11, 2011, now abandoned.

(60) Provisional application No. 61/393,190, filed on Oct. 14, 2010.

(51) Int. Cl.
*A61K 35/36* (2015.01)
*C12Q 1/02* (2006.01)
*A61K 35/32* (2015.01)
*A61K 35/76* (2015.01)
*G01N 33/50* (2006.01)

(52) U.S. Cl.
CPC .............. *C12Q 1/025* (2013.01); *A61K 35/32* (2013.01); *A61K 35/36* (2013.01); *A61K 35/76* (2013.01); *G01N 33/5082* (2013.01); *G01N 2333/07* (2013.01)

(58) Field of Classification Search
None
See application file for complete search history.

(56) References Cited

U.S. PATENT DOCUMENTS

| 4,985,254 | A | 1/1991 | Konishi |
| 5,013,558 | A | 5/1991 | Konishi |
| 5,057,324 | A | 10/1991 | Shibayama et al. |
| 5,534,509 | A | 7/1996 | Konishi et al. |
| 5,560,935 | A | 10/1996 | Konishi et al. |
| 6,051,613 | A | 4/2000 | Ohno et al. |
| 6,165,515 | A | 12/2000 | Matsuyama et al. |
| 6,238,665 | B1 | 5/2001 | Naiki |
| 6,251,929 | B1 | 6/2001 | Naiki et al. |
| 6,365,192 | B1 | 4/2002 | Konishi |
| 6,440,978 | B2 | 8/2002 | Yoshii et al. |
| 6,451,831 | B1 | 9/2002 | Ienaga et al. |
| 7,148,012 | B2 | 12/2006 | Nishioka |
| 7,238,487 | B2 | 7/2007 | Nishioka |
| 7,435,547 | B2 | 10/2008 | Nishioka |
| 7,556,649 | B2 | 7/2009 | Moehlenbruck et al. |
| 8,293,280 | B2 | 10/2012 | Ansari et al. |
| 8,338,108 | B2 | 12/2012 | Nakamura et al. |
| 2006/0051376 | A1 | 3/2006 | Nishioka |
| 2006/0134646 | A1 | 6/2006 | Ansari et al. |
| 2006/0263388 | A1 | 11/2006 | Nishioka |
| 2007/0218037 | A1 | 9/2007 | Nishioka |
| 2010/0048408 | A1 | 2/2010 | Naiki et al. |
| 2011/0111051 | A1 | 5/2011 | Oishi et al. |
| 2012/0135083 | A1 | 5/2012 | Kurohashi et al. |
| 2013/0028982 | A1 | 1/2013 | Tamaki |

FOREIGN PATENT DOCUMENTS

| CN | 1205233 A | 1/1999 |
| CN | 1237632 A | 12/1999 |
| CN | 101528947 | 9/2007 |
| EP | 2 191 836 | 6/2010 |
| JP | 53-101515 | 9/1978 |
| JP | 55-87724 | 7/1980 |
| JP | 1-265028 | 10/1989 |
| JP | 1-319422 | 12/1989 |
| JP | 2-28119 | 1/1990 |
| JP | 7-97336 | 4/1995 |
| JP | 8-291077 | 11/1996 |
| JP | 10-194978 | 7/1998 |
| JP | 11-80005 | 3/1999 |
| JP | 11-139977 | 5/1999 |
| JP | 2000-16942 | 1/2000 |
| JP | 2000-336034 | 12/2000 |
| JP | 2004-300146 | 10/2008 |
| WO | 2004/039383 | 5/2004 |
| WO | WO06065947 | 6/2006 |
| WO | 2009/028605 | 3/2009 |
| WO | 2012-051173 | 4/2012 |

OTHER PUBLICATIONS

Homer et al. (2002) SPINE 27(10): 1018-1028. (Year: 2002).*
Nakamura et al. (1990) Brain Research Bulletin, vol. 24, pp. 811-817. (Year: 1990).*
Otero et al. (2005) Methods Mol. Med. 107: 69-95. (Year: 2005).*
Poiraudeau et al. (1999) SPINE, vol. 24, No. 9, 837-844. (Year: 1999).*
Poiraudeau et al. (1999) SPINE vol. 24, No. 9, pp. 837-844. (Year: 1999).*
Loty et al. (1998) J. Biomed. Mater. Res. 42, 213-222. (Year: 1998).*
Horino et al. (2002) Life Sciences 71: 3031-3045. (Year: 2002).*

(Continued)

*Primary Examiner* — Terry A McKelvey
*Assistant Examiner* — Russell G Fiebig
(74) *Attorney, Agent, or Firm* — Greenblum & Bernstein, P.L.C.

(57) ABSTRACT

The synthesis of collagen and proteoglycan in chondrocytes, such as intervertebral disc cells, articular chondrocytes and meniscal cells is promoted by administration of an extract from inflamed tissue inoculated with vaccinia virus.

1 Claim, 4 Drawing Sheets

(56) References Cited

OTHER PUBLICATIONS

Homer et al. (2002) SPINE, vol. 27, No. 10, pp. 1018-1028 (Year: 2002).*
Gruber et al. (1997) Experimental Cell Research, 235: 13-21. (Year: 1997).*
Baer et al. (2001) J. Orthopaedic Res. 19: 2-10. (Year: 2001).*
Makoto Tamaki, "Mansei Hi Saikinsei Zenritsusen'en ni Taisuru Neurotropin no Yukosei Hokoku", The Japanese Journal of Urology, vol. 101 No. 2, Feb. 20, 2010, p. 196 (230).
"Drugs in Japan, Ethical Drugs", Japan Pharmaceutical Information Center, 1994, pp. 1434-1435.
Kawamura et al. (1998) Life Sciences, vol. 62, No. 24, pp. 2181-2190.
Urban et al., (2003) Arthritis Research and Therapy vol. 5, No. 3. 120-130.
Higashiguchi (1990) Folia Pharmacologica Japonica 96 (4): 153-161.
Document entitled "Low Back Pain", NIH Publication No. 15-5161, Dec. 2014.
International Search Report from PCT/US2011/055757 dated Feb. 27, 2012.
Sep. 10, 2013 International Preliminary Report on Patentability with Feb. 27, 2012 Written Opinion from PCT/US2011/055757.
Vernillo et al, "Stimulation of collagen and glycosaminoglycan production by phenytoin 5,5-diphenylhydantoin in monolayer cultures of mesenchymal cells derived from embryonic chick sternae," *Archives of Oral Biology* vol. 31, Issue 12, 1986, pp. 819-823.
Ienaga et al, "Bioactive Compounds Produced in Animal Tissue (II); Two Hydantoin Plant growth Regulators Isolated From Inflamed Rabbit Skin Tissue," Tetrahedron Letters, vol. 28, No. 39, pp. 4587-4588 (1987).
Chinese Office Action with English Translation in respect to Chinese Application No. 201180049567.2, dated May 26, 2014.
Chinese Office Action with English Translation in respect to Chinese Application No. 201180049567.2, dated Dec. 2, 2014.
Extended European Search Report in respect to European Application No. 11833245.1, dated Jul. 9, 2014.
Australian Patent Examination Report in respect to Australian Application No. 2011316756, dated Sep. 15, 2014.
Chinese Journal of Pain Medicine, vol. 10, No. 1, pp. 56-58, with English Abstract.
Chinese Journal of Birth Health & Heredity, vol. 16, No. 7, pp. 3, 4, and 8, with English Abstract.
Chinese Journal of Prosthodontics, vol. 2, No. 3, pp. 192-195 and 198, with English Abstract.
Folia Pharmacologica Japonica, vol. 96, No. 4, 1990, pp. 153-162, with English Abstract at the end.
Journal of Neurosurgery Spine, Nov. 2008, vol. 9, No. 5, pp. 411-418.
Journal of Pharmacological Sciences, vol. 97, No. 3, pp. 429-436.
Collagen from Wikipedia (http://wikipedia.org/wiki/collagen), 13 pages, downloaded from internet Feb. 27, 2015.
Procollagen-definition of procollagen by Medical dictionary (http://medical-dictionary.thefreedictionary.com/procollagen), 2 pages, downloaded from internet Feb. 27, 2015.
"Evidence Showing Layers of yaline Cartilage in Adult Human Intervertebral Disk and Bone Junction (Important)," Natural Height Growth, (http://www.naturalheightgrowth.com/2013/02/12/evidence-showing-layers-of-hyaline-cartilage-in-adult-human-intervertebral-disk-and-bone-junction-important), May 12, 2013, 5 pages, downloaded from internet Mar. 2, 2015.
Japanese Office Action with English Translation in respect to Japanese Application No. 2013-533935, dated Sep. 4, 2015.
"Clinical Condition and Treatment of Disc Herniation", vol. 12, No. 3, 2000, pp. 463 with English Abstract.
J. Jpn. Orthop. Assoc., vol. 79, No. 8, 2005, pp. S735.

* cited by examiner

METHOD FOR PROMOTING THE SYNTHESIS OF COLLAGEN AND PROTEOGLYCAN IN CHONDROCYTES

CROSS-REFERENCE TO RELATED APPLICATIONS

The present application is a divisional application of U.S. application Ser. No. 13/821,617, which is a National Stage of International Patent Application No. PCT/US11/55757, filed Oct. 11, 2011, which claims benefit of U.S. Provisional Application No. 61/393,190, filed Oct. 14, 2010. The entire disclosures of these applications are expressly incorporated by reference herein.

FIELD OF THE INVENTION

The present invention relates to a novel medical use of an extract from inflamed tissue inoculated with vaccinia virus, and in particular, relates to a method for promoting the synthesis of collagen and proteoglycan in chondrocytes, such as intervertebral disc cells, articular chondrocytes and meniscal cells.

BACKGROUND OF THE INVENTION

A medical agent, which has been sold under the brand name of "Neurotropin", contains a nonprotein extract from the inflamed skin of rabbits following inoculation with vaccinia virus as an active ingredient. Neurotropin (NTP) has been widely used to treat neuropathic pain, including post-herpetic neuralgia and low back pain in Japan. In animal models, NTP has been shown that the anti-nociceptive effect was derived by the activation of the descending monoaminergic pain inhibitory system. NTP has also been shown to inhibit the pain pathway by inhibiting activation of the kallikrein-kinin cascade and, consequently, the formation of bradykinin in vitro and in vivo.

The suppressive effect of NTP on tumor necrosis factor-$\alpha$ (TNF-$\alpha$) and cyclooxygenase-2 (COX-2) mRNA expression by human intervertebral disc cells was recently reported. However, it is not clear if NTP has an effect on intervertebral disc cell extracellular matrix (ECM) synthesis.

SUMMARY OF THE INVENTION

An extract from inflamed tissue inoculated with vaccinia virus is employed to promote the synthesis of collagen and proteoglycan in chondrocytes, such as intervertebral disc cells, such as bovine nucleus pulposus cells or annulus fibrosus cells, articular chondrocytes and meniscal cells. In an aspect of the invention, there is provided a method for promoting the synthesis of proteoglycan and/or collagen in chondrocytes in a patient, comprising administering to a patient in need of such treatment a pharmaceutically effective amount of an extract isolated from inflamed tissue inoculated with vaccinia virus. In another aspect of the present invention there is provided a method for regenerating a chondrocyte extracellular matrix, comprising administering to a patient in need of such treatment an extract isolated from inflamed tissue inoculated with vaccinia virus.

BRIEF DESCRIPTION OF THE DRAWINGS

The present invention is further illustrated by the accompanying drawings wherein.

DETAILED DESCRIPTION OF THE INVENTION

This invention is based on the results to assess the effects of NTP on proteoglycan (PG) and collagen synthesis using bovine nucleus pulposus (NP) and anulus fibrosus (AF) cells cultured in alginate beads under normoxic and hypoxic conditions.

As for the extract from inflamed tissue inoculated with vaccinia virus of the present invention, there are various reports on physiological active substances produced in the inflamed tissue inoculated with vaccinia virus, the method for extracting the substances from the diseased tissue, the pharmacological activities and the like as previously reported (see paragraph [0008] of WO 2009/028605, and EP2191836, and Japanese Patent Application Publication Nos. JP-A-53-101515, JP-A-55-87724, JP-A-1-265028, JP-A-1-319422, JP-A-2-28119, JP-A-7-97336, JP-A-8-291077, JP-A-10-194978, JP-A-11-80005, JP-A-11-139977, JP-A-2000-336034, JP-A-2000-16942, and JP-A-2004-300146, and International Publication No. WO 2004/039383.)

Furthermore, a preparation of an extract from inflamed skins of rabbits inoculated with vaccinia virus is commercially available as a pharmaceutical product, and may be employed in the present invention. The preparation, as described in pages 2978 to 2980 of "Drugs in Japan, Ethical Drugs" (2010, edited and published by Japan Pharmaceutical Information Center), is a medicinal agent containing non-proteinous active substances extracted and separated from the inflamed skin tissue of rabbits inoculated with vaccinia virus. The preparation is known to be effective against low back pain, cervicobrachial syndrome, symptomatic neuralgia, periarthritis scapulohumeralis, osteoarthritis, itchiness accompanied with skin diseases (eczema, dermatitis, urticaria), allergic rhinitis, sequelae of subacute myelo-optico-neuropathy such as coldness, paresthesia and pain, postherpetic neuralgia and the like. The preparation is approved as an ethical drug in the form of hypodermic, intramuscular and intravenous injection products and of tablets and is commercially available.

The extract from inflamed tissue inoculated with vaccinia virus used in the present invention is a non-proteinous biofunction-regulating substance extracted from the inflamed tissue inoculated with vaccinia virus as described above, and the preparation of the extracted solution from inflamed skins of rabbits inoculated with vaccinia virus listed in the "Drugs in Japan, Ethical Drugs" is approved as a pharmaceutical product and is commercially available. In addition, various extracts from inflamed tissue inoculated with vaccinia virus described in Patent Documents described above may be used as the substance of the present invention, and their producing methods, suitable doses and the like are also given in the documents.

The extract from inflamed tissue inoculated with vaccinia virus of the present invention can be obtained in the following manner: inflamed tissue inoculated with vaccinia virus is crushed; an extraction solvent is added to remove the tissue fragments; then deproteinization is carried out; the deproteinized solution is adsorbed onto an adsorbent; and then the active ingredient is eluted.

The extract from inflamed tissue inoculated with vaccinia virus is produced, for example, according to the following process.

(a) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(b) The pH of the extraction liquid is adjusted to an acidic condition and the liquid is heated for deproteinization. Then, the deproteinized solution is adjusted to an alkaline condition, heated, and then filtered or centrifuged.

(c) The obtained filtrate or supernatant is made acidic and adsorbed onto an adsorbent such as activated carbon or kaolin.

(d) To the adsorbent, an extraction solvent such as water is added, the pH is adjusted to an alkaline condition, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that are infected with vaccinia virus such as rabbits, cows, horses, sheep, goats, monkeys, rats or mice can be used, and preferred inflamed tissues are inflamed skin tissues of rabbits.

The inflamed tissues are collected and crushed, and 1 to 5 volumes of extraction solvent is added to make an emulsified suspension. As for the extraction solvent, distilled water, physiological saline, weakly acidic to weakly basic buffer and the like can be used, and stabilizers such as glycerin, antibacterial/antiseptic agents such as phenol, and salts such as sodium chloride, potassium chloride or magnesium chloride may be suitably added. At this time, the extraction may be facilitated by breaking the cellular tissues with treatment such as freezing and thawing, ultrasonic waves, cell membrane dissolving enzymes or surfactants.

The obtained emulsified extraction liquid is subjected to filtration, centrifugation or the like to remove tissue fragments, and then deproteinized. The deproteinization operation may be carried out by a generally known method, for example, heat treatment, treatment with a protein denaturant such as an acid, base, urea and guanidine, treatment with an organic solvent such as acetone, isoelectric precipitation, and salting out can be applied. Then, by a general method for removing insolubles such as filtration using filter paper (for example, cellulose or nitrocellulose), glass filters, Celite, Seitz filters or the like, ultrafiltration and centrifugation, the precipitated insoluble protein is removed.

The extraction liquid containing active ingredients obtained in this manner is acidified, preferably adjusted to pH 3.5 to 5.5 with an acid such as hydrochloric acid, sulfuric acid or hydrobromic acid, and then adsorbed onto an adsorbent. Examples of the usable adsorbent include activated carbon and kaolin. The adsorbent may be added into the extraction liquid with stirring, or the extraction liquid may be passed through a column filled with the adsorbent to adsorb the active ingredients onto the adsorbent. When the adsorbent is added into the extraction liquid, the solution is removed by filtration, centrifugation, or the like to obtain the adsorbent in which the active ingredients are adsorbed.

In order to elute (desorb) the active ingredients from the adsorbent, an elution solvent is added to the adsorbent to elute at room temperature or with suitable heating or with stirring, and the adsorbent is removed by a general method such as filtration, centrifugation, or the like. As for the elution solvent to be used, a basic solvent such as water, methanol, ethanol or isopropanol that are adjusted to have a basic pH or a suitable mixture thereof may be used, and preferably water adjusted to pH 9 to 12 may be used.

The extract (eluate) obtained in this manner may be properly prepared in a suitable form as a raw material for a formulation or a pharmaceutical formulation. For example, the solution may be adjusted to have a nearly neutral pH to be a raw material for a formulation, and may be adjusted to have a desired concentration by concentration or dilution. In addition, for a formulation for injection, sodium chloride may be added to prepare a solution isotonic to physiological saline. Furthermore, the solution may be concentrated to dryness or freeze-dried to prepare a solid form available for the raw material of tablets or the like.

Examples of an administration method to a patient in need of treatment include oral and other administrations such as subcutaneous, intramuscular and intravenous administrations, in pharmaceutically effective amounts. The dose can be suitably determined depending on the type of extract from inflamed tissues inoculated with vaccinia virus. The dose that is approved in the commercially available preparation according to the "Drugs in Japan, Ethical Drugs" (page 2978) is principally 16 NU per day by oral administration and 3.6 to 7.2 NU per day by injection as an ethical drug. However, the dose may be appropriately increased or decreased depending on the type of disease, degree of seriousness, individual difference in the patients, method of administration, period of administration and the like (NU: Neurotropin unit. Neurotropin unit is defined by $ED_{50}$ value of analgesic effect measured by a modified Randall-Selitto method using SART-stressed mice that are chronic stressed animals showing a lowered pain threshold than normal animals. One NU indicates the activity of 1 mg of analgesic ingredients in Neurotropin preparations when the $ED_{50}$ value is 100 mg/kg of the preparation).

Hereinafter presented are examples of methods for producing an extract from inflamed tissues inoculated with vaccinia virus as well as results of a pharmacological test concerning novel pharmacological activity of the extract, that is, the promoting activity on the synthesis of collagen and proteoglycan in intervertebral disc cells. The present invention is not intended to be limited to the descriptions in the following Examples, where all parts, percentages, and ratios are by weight, all temperatures are in ° C., and all pressures are atmospheric unless indicated to the contrary:

Example 1

Skins of healthy adult rabbits were inoculated with vaccinia virus. The inflamed skins were removed and crushed, and to the crushed skins, phenolated water was added. Then, the mixture was filtered under pressure, and the obtained filtrate was adjusted to pH 5 with hydrochloric acid, and then heated at 90 to 100° C. for 30 minutes. After deproteinization by filtration, the filtrate was adjusted to pH 9 with sodium hydroxide, further heated at 90 to 100° C. for 15 minutes, and then filtered. The filtrate was adjusted to about pH 4.5 with hydrochloric acid, and 2% activated carbon was added. The mixture was stirred for 2 hours and then centrifuged. To the collected activated carbon, water was added. The mixture was adjusted to pH 10 with sodium hydroxide, stirred at 60° C. for 1.5 hours, and then centrifuged and filtered to obtain a supernatant. To the collected activated carbon, water was added again. The mixture was adjusted to pH 11 with sodium hydroxide, stirred at 60° C. for 1.5 hours, and then centrifuged to obtain a supernatant. The two supernatants were combined and neutralized with hydrochloric acid to obtain an extract from inflamed skins of rabbits inoculated with vaccinia virus. In the following pharmacological tests, the extract was adjusted to an appropriate concentration to be used.

Example 2

Skins of healthy adult rabbits were inoculated with vaccinia virus to be infected. Subsequently, the inflamed skins were aseptically removed and chopped, and then phenol-added glycerin water was added. The mixture was ground with a homogenizer to be emulsified. Subsequently, the emulsion was filtered. The obtained filtrate was adjusted to weak acidity (pH 4.5 to 5.5) with hydrochloric acid, then heated at 100° C. and filtered. The filtrate was adjusted to weak alkalinity (pH 8.5 to 10.0) with sodium hydroxide, further heated at 100° C. and then filtered. The filtrate was adjusted to about pH 4.5 with hydrochloric acid, and about 1.5% activated carbon was added. The mixture was stirred for 1 to 5 hours and then filtered. To the activated carbon collected by the filtration, water was added. The mixture was adjusted to pH 9.4 to 10 with sodium hydroxide, stirred for 3 to 5 hours, and then filtered. The filtrate was neutralized with hydrochloric acid.

Example 3

Next, an example of the pharmacological test results concerning promoting activity on the synthesis of collagen and proteoglycan in intervertebral disc cells in which the extract from inflamed tissue inoculated with vaccinia virus (NTP) of the present invention obtained in Example 1 was used as a test substance, is shown. The effect of NTP on proteoglycan (PG) and collagen synthesis and cell proliferation in intervertebral disk cells is given below and in FIGS. 1-4.

1. Materials and Methods

Bovine nucleus pulposus (NP) and anulus fibrosus (AF) cells, isolated from 14-18 month-old bovine coccygeal intervertebral discs, were encapsulated in alginate (4E+6 cells/mL) and cultured for 11 days in DMEM/F12 with 10% fetal bovine serum (FBS) under normoxic (21% $O_2$) or hypoxic (5% $O_2$) conditions. These cultures were treated with three different concentrations (0.001 NU/ml, 0.01 NU/mL, and 0.1 NU/mL) of NTP for three days. To assess the synthesis of PGs and collagen, the cultures were labeled with $^{35}$S-sulfate or $^{3}$H-proline during the last 4 or 16 hours, respectively. The beads and media were collected and digested by papain after labeling, as previously described [Masuda, K. et al., 3 Orthop Res., 21, 922-930 (2003) and Akeda, K, Spine, 31, 959-966 (2006)], and the radioactive precursor incorporation was measured in media and alginate beads separately. Cell proliferation was assessed using the CellTiter 96 Aqueous One Solution Cell Proliferation Assay (Promega, Madison, Wis.). All data from three experiments from different batches of cells were normalized with the average value of the control group in each experiment. The effects of treatment were assessed using ANOVA with PSLD test as a posthoc test.

2. Results

1) Cell Proliferation

The oxygen concentration and treatment with NTP did not affect NP and AF cell proliferation at both the 7 and 14 days time points.

2) PG Synthesis

Figure 1:
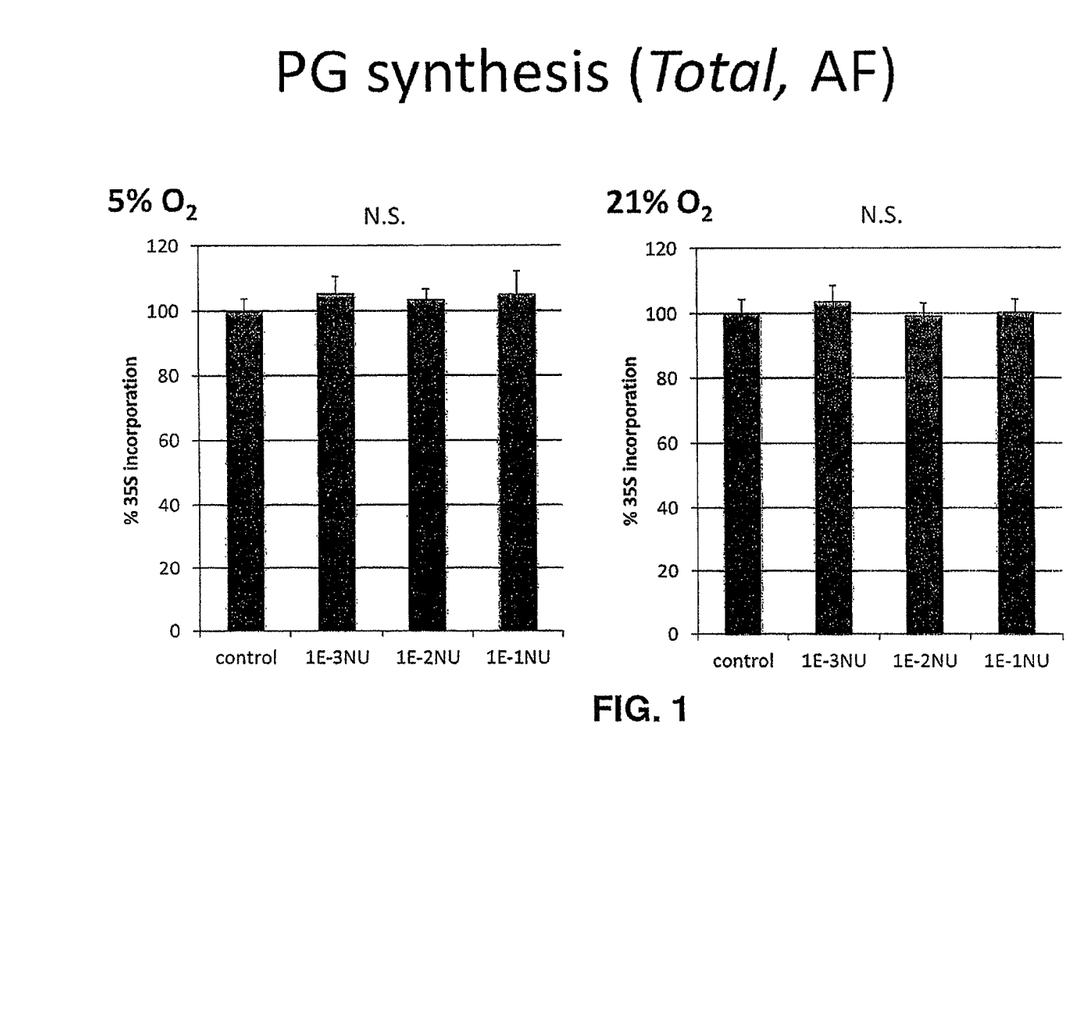
FIG. 1 is an experimental result of an activity on the synthesis of proteoglycan in intervertebral disc cells which are anulus fibrosus cells (AF) of an extract from inflamed tissue inoculated with vaccinia virus.
Figure 2:
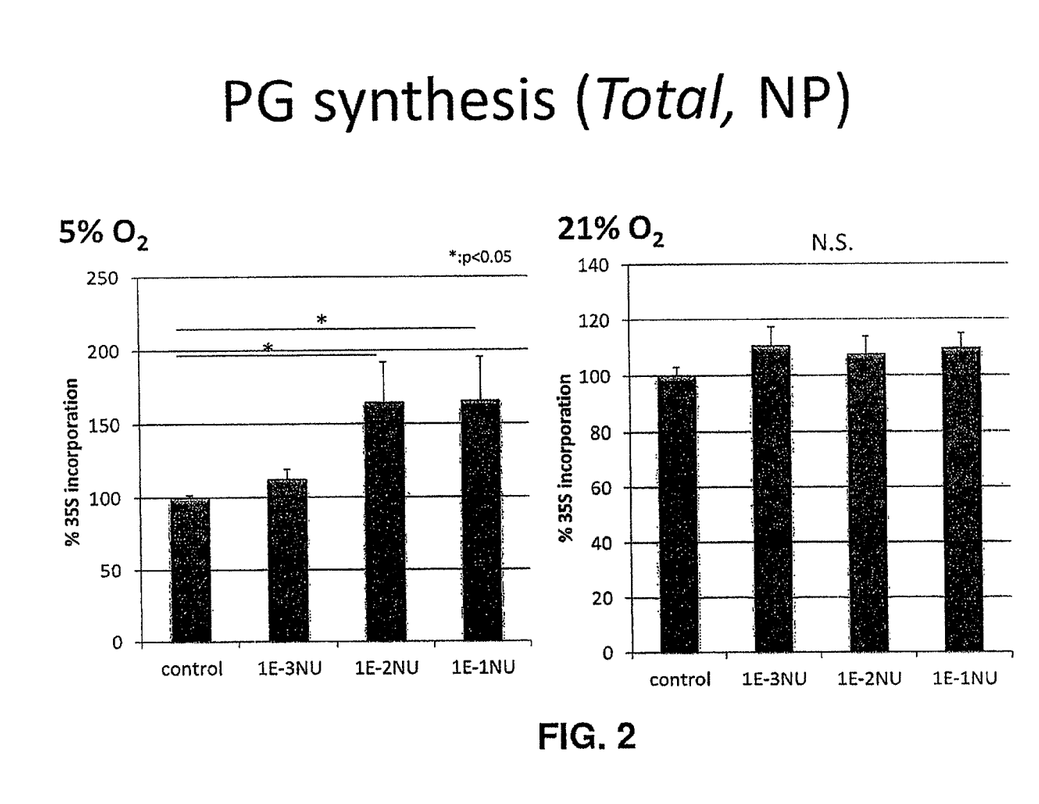
FIG. 2 is an experimental result of an activity on the synthesis of proteoglycan in intervertebral disc cells which are bovine nucleus pulposus cells (NP) of an extract from inflamed tissue inoculated with vaccinia virus.

In NP cells, PG synthesis was significantly increased with NTP treatment under culture at 5% $O_2$ (at 0.01 NU/ml, +65%, p<0.05, at 0.1 NU/nil, +66%, p<0.05, FIG. 2). There were no significant differences in PG synthesis in NP cells under normoxic culture. As shown in FIG. 1, in AF cells, NTP did not change the level of PG synthesis under both normoxic and hypoxic conditions.

3) Collagen Synthesis

Figure 3:
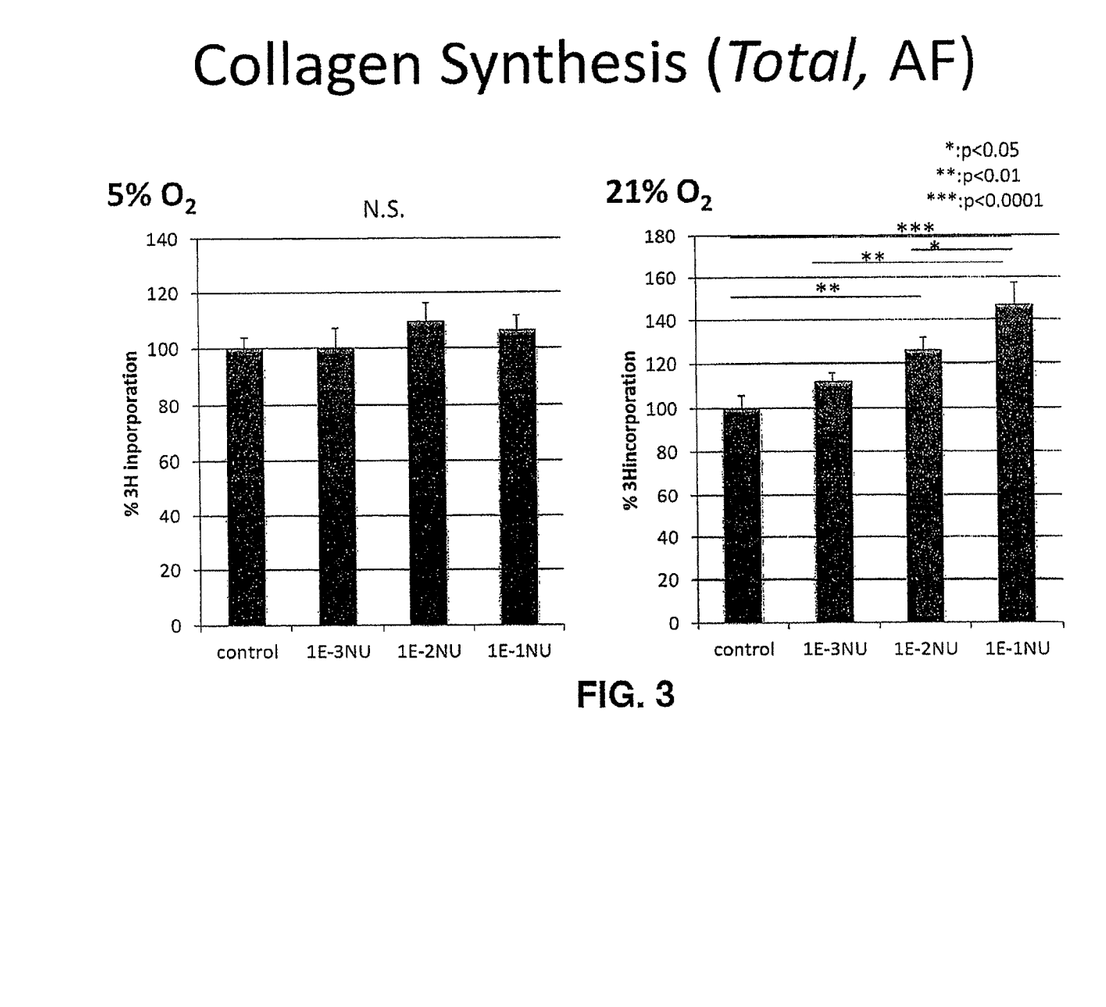
FIG. 3 is an experimental result of an activity on the synthesis of collagen in intervertebral disc cells which are anulus fibrosus cells (AF) of an extract from inflamed tissue inoculated with vaccinia virus.
Figure 4:
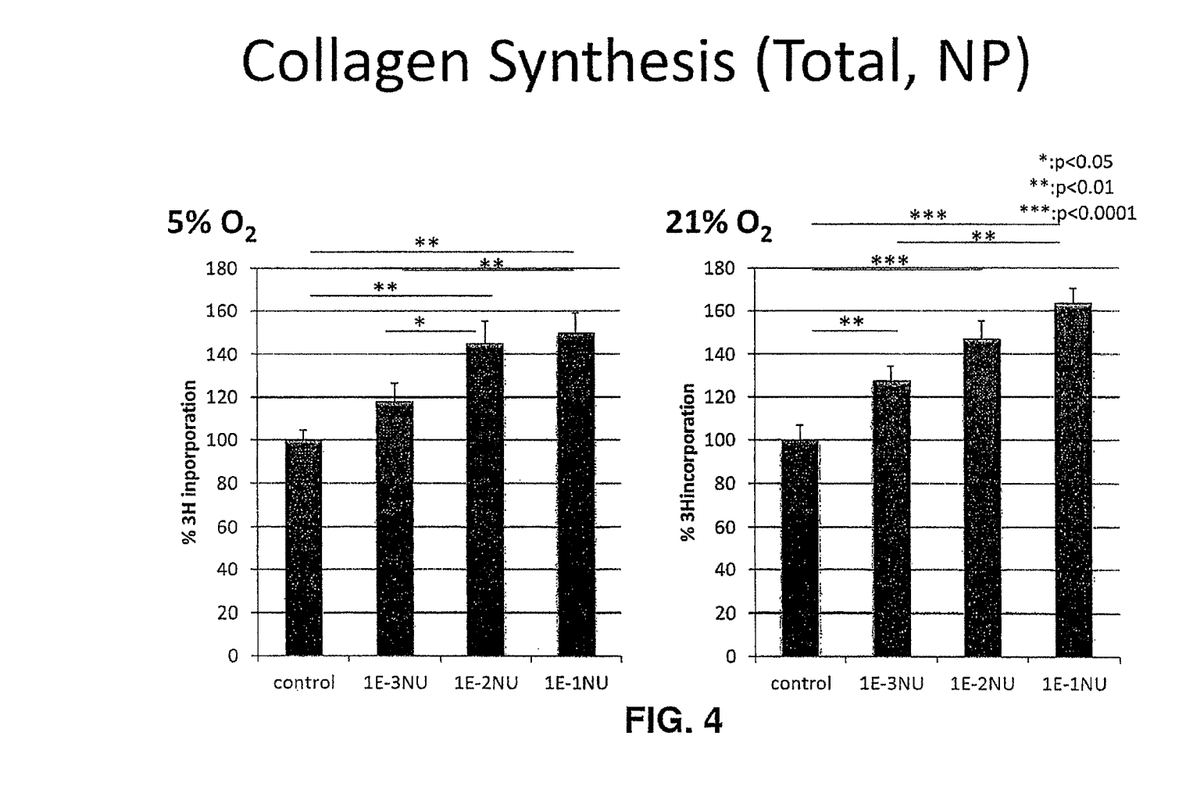
FIG. 4 is an experimental result of an activity on the synthesis of collagen in intervertebral disc cells which are bovine nucleus pulposus cells (NP) of an extract from inflamed tissue inoculated with vaccinia virus.

Collagen synthesis by NP cells in under 5% $O_2$ and NP and AF cells under 21% $O_2$ was increased by treatment with NTP in a dose-dependent manner, as shown in FIGS. 3 and 4 (maximum stimulation at 0.1 NU/ml: NP, 5% $O_2$, +50%; NP, 21% $O_2$, +63%; AF, 21% $O_2$+47%).

As shown above, this study has shown for the first time that NTP can stimulate the extracellular matrix synthesis of intervertebral disc cells. Interestingly, the effect of NTP on PG synthesis by NP cells was more apparent under 5% $O_2$ than under 21% $O_2$ culture conditions. Considering the hypoxic condition of the NP in vivo, these results may suggest that NP cells can respond to NTP under physiologically relevant conditions. Although the positive effects of NIP on collagen synthesis by NP cells were observed in both 5% $O_2$ and 21% $O_2$, stimulation in the AF was only observed in the 21% $O_2$ condition. Unlike the increased synthesis of PGs by NP cells in response to NTP, AF cells were more responsive to NTP under the 21% $O_2$ condition. Because oxygen tension is significantly higher in the AF than in the NP, the greater response of AF cells to NTP at 21% $O_2$ may also reflect optimal culture conditions.

Chondrocytes are present in various cartilages such as articular cartilage, intervertebral disc, meniscus, etc. The chondrocytes produce an extracellular matrix around them with cell divisions to make cartilage formation. Cartilages are classified into groups of hyaline cartilage, elastic cartilage and fibro cartilage according to the content ratio of amorphous matrix and fibrous material. The main components of the extracellular matrix are collagen and proteoglycan. Since NTP has a promoting activity on the synthesis of collagen and proteoglycan in chondrocytes such as intervertebral disc cells, it is indicated that NTP has a regenerating activity on a chondrocyte extracellular matrix of various cartilages.

INDUSTRIAL APPLICABILITY

The present invention relates to a novel medical use of an extract from inflamed tissue inoculated with vaccinia virus, and in particular, relates to a method for promoting the synthesis of collagen and proteoglycan in chondrocytes, such as intervertebral disc cells, articular chondrocytes and meniscal cells. Preferred embodiments of the present invention are given as follows:

1. A method for promoting the synthesis of proteoglycan and/or collagen in chondrocytes in a patient, comprising 
administering to a patient in need of such treatment an extract isolated from inflamed tissue inoculated with vaccinia virus.

2. An agent for promoting the synthesis of proteoglycan and/or collagen in chondrocytes containing an extract isolated from inflamed tissue inoculated with vaccinia virus.

3. A use of an extract isolated from inflamed tissue inoculated with vaccinia virus for promoting the synthesis of proteoglycan and/or collagen in chondrocytes.

4. A method for determining or evaluating an extract isolated from inflamed tissue inoculated with vaccinia virus wherein a promoting activity on the synthesis of proteoglycan and/or collagen in cultured chondrocytes is used as an index.

5. An extract isolated from inflamed tissue inoculated with vaccinia virus having a promoting activity on the synthesis of proteoglycan and/or collagen in chondrocytes.

6. A method for regenerating a chondrocyte extracellular matrix, comprising administering to a patient in need of such treatment an extract isolated from inflamed tissue inoculated with vaccinia virus.

7. An agent for regenerating a chondrocyte extracellular matrix containing an extract isolated from inflamed tissue inoculated with vaccinia virus.

8. Use of an extract isolated from inflamed tissue inoculated with vaccinia virus for regenerating a chondrocyte extracellular matrix.

9. A method for determining or evaluating an extract isolated from inflamed tissue inoculated with vaccinia virus wherein a regenerating activity of a chondrocyte extracellular matrix is used as an index.

10. An extract isolated from inflamed tissue inoculated with vaccinia virus having a regenerating activity of a chondrocyte extracellular matrix.

11. A method for promoting the synthesis of proteoglycan in intervertebral disc cells (bovine nucleus pulposus cells), comprising administering to a patient in need of such treatment an extract isolated from inflamed tissue inoculated with vaccinia virus.

12. A method for promoting the synthesis of collagen in intervertebral disc cells (bovine nucleus pulposus cells or anulus fibrosus cells), comprising administering to a patient in need of such treatment an extract isolated from inflamed tissue inoculated with vaccinia virus.

13. An agent for promoting the synthesis of proteoglycan in intervertebral disc cells (bovine nucleus pulposus cells) containing an extract isolated from inflamed tissue inoculated with vaccinia virus.

14. An agent for promoting the synthesis of collagen in intervertebral disc cells (bovine nucleus pulposus cells or anulus fibrosus cells) containing an extract isolated from inflamed tissue inoculated with vaccinia virus.

15. Use of an extract isolated from inflamed tissue inoculated with vaccinia virus for promoting the synthesis of proteoglycan in intervertebral disc cells (bovine nucleus pulposus cells).

16. Use of an extract isolated from inflamed tissue inoculated with vaccinia virus for promoting the synthesis of collagen in intervertebral disc cells (bovine nucleus pulposus cells or anulus fibrosus cells).

17. A method for determining or evaluating an extract isolated from inflamed tissue inoculated with vaccinia virus wherein a promoting activity on the synthesis of proteoglycan in cultured intervertebral disc cells (bovine nucleus pulposus cells) is used as an index.

18. A method for determining or evaluating an extract isolated from inflamed tissue inoculated with vaccinia virus wherein a promoting activity on the synthesis of collagen in cultured intervertebral disc cells (bovine nucleus pulposus cells or anulus fibrosus cells) is used as an index.

19. An extract isolated from inflamed tissue inoculated with vaccinia virus having a promoting activity on the synthesis of proteoglycan in intervertebral disc cells (bovine nucleus pulposus cells).

20. An extract isolated from inflamed tissue inoculated with vaccinia virus having a promoting activity of collagen synthesis in intervertebral disc cells (bovine nucleus pulposus cells or anulus fibrosus cells).

21. A method for regenerating an intervertebral disc cell extracellular matrix, comprising administering to a patient in need of such treatment an extract isolated from inflamed tissue inoculated with vaccinia virus.

22. An agent for regenerating an intervertebral disc cell extracellular matrix containing an extract isolated from inflamed tissue inoculated with vaccinia virus.

23. Use of an extract isolated from inflamed tissue inoculated with vaccinia virus for regenerating an intervertebral disc cell extracellular matrix.

24. A method for determining or evaluating an extract isolated from inflamed tissue inoculated with vaccinia virus wherein a regenerating activity of an intervertebral disc cell extracellular matrix is used as an index.

25. An extract isolated from inflamed tissue inoculated with vaccinia virus having a regenerating activity of an intervertebral disc cell extracellular matrix.

26. A method for treating or preventing degenerative intervertebral discs, comprising administering to a patient in need of such treatment an extract isolated from inflamed tissue inoculated with vaccinia virus.

27. An agent for treating or preventing degenerative intervertebral discs containing an extract isolated from inflamed tissue inoculated with vaccinia virus.

28. Use of an extract isolated from inflamed tissue inoculated with vaccinia virus for treating or preventing degenerative intervertebral discs.

29. A method for treating or preventing a pain caused by intervertebral disc degeneration, wherein an intervertebral disc cell extracellular matrix is regenerated by administering to a patient in need of such treatment an extract isolated from inflamed tissue inoculated with vaccinia virus.

30. A method for treating or preventing a pain caused by intervertebral disc degeneration, wherein the synthesis of proteoglycan in intervertebral disc cells (bovine nucleus pulposus cells) is promoted by administering to a patient in need of such treatment an extract isolated from inflamed tissue inoculated with vaccinia virus.

31. A method for treating or preventing a pain caused by intervertebral disc degeneration, wherein the synthesis of collagen in intervertebral disc cells (bovine nucleus pulposus cells or anulus fibrosus cells) is promoted by administering to a patient in need of such treatment an extract isolated from inflamed tissue inoculated with vaccinia virus.

32. The embodiments as described above in any one of subparagraphs 1 to 31 wherein the inflamed tissue is a rabbit skin tissue.

What is claimed is:

1. A method for determining or evaluating the promoting effect of an extract isolated from a rabbit skin inflamed by inoculation with vaccinia virus on synthesis of proteoglycan and/or collagen comprising:

a) treating cultured nucleus pulposus cells under hypoxic conditions with an effective amount of the extract to promote synthesis of proteoglycan in the cultured nucleus pulposus cells, and measuring a promoting activity on the synthesis of proteoglycan in the cultured nucleus pulposus cells by said extract, or
b) treating cultured nucleus pulposus cells and/or cultured anulus fibrosus cells under normoxic conditions with an effective amount of the extract to promote synthesis of collagen in the cultured nucleus pulposus cells and/or anulus fibrosus cells, and measuring a promoting activity on the synthesis of collagen in the cultured nucleus pulposus cells and/or anulus fibrosus cells by said extract, or
c) treating cultured nucleus pulposus cells under hypoxic conditions with an effective amount of the extract to promote synthesis of collagen in the cultured nucleus pulposus cells, and measuring a promoting activity on the synthesis of collagen in the cultured nucleus pulposus cells by said extract.

* * * * *

UNITED STATES PATENT AND TRADEMARK OFFICE
CERTIFICATE OF CORRECTION

PATENT NO. : 10,711,292 B2
APPLICATION NO. : 14/858396
DATED : July 14, 2020
INVENTOR(S) : Koichi Masuda et al.

Page 1 of 1

It is certified that error appears in the above-identified patent and that said Letters Patent is hereby corrected as shown below:

On the Title Page

Column 1, item (73) Assignees, which read:
"(73) Assignees: NIKKON ZOKI PHARMACEUTICAL CO., LTD., Osaka (JP); THE REGENTS OF THE UNIVERSITY OF CALIFORNIA, Oakland CA (US)"

Should read:
--(73) Assignees: NIPPON ZOKI PHARMACEUTICAL CO., LTD., Osaka (JP); THE REGENTS OF THE UNIVERSITY OF CALIFORNIA, Oakland CA (US)--

Signed and Sealed this
Sixth Day of October, 2020

Andrei Iancu
*Director of the United States Patent and Trademark Office*